(12) United States Patent
Beck

(10) Patent No.: US 10,736,538 B2
(45) Date of Patent: Aug. 11, 2020

(54) METHOD AND COMPUTER DIFFERENTIATING CORRELATION PATTERNS IN FUNCTIONAL MAGNETIC RESONANCE IMAGING

(71) Applicant: Siemens Healthcare GmbH, Erlangen (DE)

(72) Inventor: Thomas Beck, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 154 days.

(21) Appl. No.: 15/983,442

(22) Filed: May 18, 2018

(65) Prior Publication Data

US 2018/0333068 A1    Nov. 22, 2018

(30) Foreign Application Priority Data

May 19, 2017 (EP) .................. 17172018

(51) Int. Cl.

| A61B 5/055 | (2006.01) |
|---|---|
| G01R 33/48 | (2006.01) |
| G06T 7/00 | (2017.01) |
| A61B 5/00 | (2006.01) |
| G06K 9/20 | (2006.01) |
| G06K 9/62 | (2006.01) |
| G01R 33/56 | (2006.01) |

(52) U.S. Cl.
CPC ............ *A61B 5/055* (2013.01); *A61B 5/0042* (2013.01); *A61B 5/40* (2013.01); *G01R 33/4806* (2013.01); *G01R 33/5601* (2013.01); *G06K 9/2018* (2013.01); *G06K 9/6271* (2013.01); *G06T 7/0012* (2013.01); *A61B 2576/026* (2013.01); *G06K 2209/051* (2013.01); *G06T 2207/10088* (2013.01); *G06T 2207/30016* (2013.01)

(58) Field of Classification Search
None
See application file for complete search history.

(56) References Cited

U.S. PATENT DOCUMENTS

| 2017/0188862 A1* | 7/2017 | Kale ................. A61B 5/0404 |
| 2018/0130207 A1* | 5/2018 | Anderson ............. G16H 50/30 |
| 2018/0204111 A1* | 7/2018 | Zadeh ................. G06N 3/0436 |

OTHER PUBLICATIONS

Gore Ranjana Waman, Automated Classification of Schizophrenia With Neural Networks, IJCST vol. 4, Issue 1, Jan.-Mar. 2013. (Year: 2013).*

(Continued)

*Primary Examiner* — Andrae S Allison
(74) *Attorney, Agent, or Firm* — Schiff Hardin LLP

(57) ABSTRACT

A time series of image data is provided to a computer as the basis for performing an ICA to identify a number of candidate correlation patterns. The number of candidate correlation patterns includes a number of neurophysical events and false patterns due to noise. This is followed by a differentiation in the computer between the neurophysical events and the false patterns, for example based on a metric, which indicates the intensity of the candidate correlation patterns in a sub-region of the brain, or by a computer-implemented classifier. Such techniques can be used in conjunction with functional magnetic-resonance imaging.

9 Claims, 4 Drawing Sheets

(56) References Cited

OTHER PUBLICATIONS

Shen, Dinggang, Guorong Wu, and Heung-Il Suk. "Deep learning in medical image analysis." Annual review of biomedical engineering 19 (2017): 221-248. (Year: 2017).*
Josin G. M and Liddle P.F. Neural Network Analysis of the Pattern of Functional Connectivity between Cerebral Areas in Schizophrenia. Biological Cybernetics, 2001; 84, 117-122 (Year: 2001).*
Shad et al, Neurobiology of Insight Deficits in Schizophrenia: An fMRI Study, Schizophr Res. Jul. 2015 ; 165(0): 220-226. doi: 10.1016/j.schres.2015.04.021. (Year: 2015).*
Maya Bleich-Cohen, Shahar Jamshy, Haggai Sharon, Ronit Weiznnan, Nathan Intrator, Michael Poyurovsky, Talma Hendler, Machine learning fMRI classifier delineates subgroups of schizophrenia patients, Schizophrenia Research, vol. 160, Issues 1-3, 2014, (Year: 2014).*
Griswold et al., "Generalized Autocalibrating Partially Parallel Acquisitions (GRAPPA)," Magnetic Resonance in Medicine, vol. 47, pp. 1202-1210 (2002).
Rumelhart et al., "Learning representations by back-propagating errors," Nature, vol. 323, pp. 533-536 (1986).
Setsompop et al., "Blipped-Controlled Aliasing in Parallel Imaging (blipped-CAIPI) for simultaneous multi-slice EPI with reduced g-factor penalty," Magn. Reson Med., vol. 67, No. 5, pp. 1210-1224 (2012).
"FSL—ICA Practical," screenshot from Mar. 29, 2017.
Krizhevsky et al., "ImageNet Classification with Deep Convolutional Neural Networks," Advances in neural information processing systems, pp. 1-9 (2012).
Wang et al., "Dimensionality of ICA in resting-state fMRI investigated by feature optimized classification of independent components with SVM," Frontiers in Human Neuroscience, vol. 9, pp. 1-17 (2015).
Greicius et al., "Regional Analysis of Hippocampal Activation During Memory Encoding and Retrieval: fMRI Study," Hippocampus, vol. 13, pp. 164-174 (2003).
Thesen et al., "Prospective Acquisition Correction for Head Motion With Image-Based Tracking for Real-Time fMRI," Magnetic Resonance in Medicine, vol. 44, No. 3, pp. 457-465 (2000).
Lawrence et al., "Face Recognition: A Convolutional Neural-Network Approach," IEEE Transactions on Neural Networks, vol. 8, No. 1, pp. 98-113 (1997).
Salimi-Khorshidi et al., "Automatic Denoising of Functional MRI Data: Combining Independent Component Analysis and Hierarchical Fusion of Classifiers," Neuroimage, vol. 90, pp. 449-468 (2014).
Breuer et al., "Controlled Aliasing in Parallel Imaging Results in Higher Acceleration (CAIPIRINHA) for Multi-Slice Imaging," Magnetic Resonance in Medicine, vol. 53, pp. 684-691 (2005).
FslWiki—Melview, Feb. 16, 2015.
Greicius et al., "Functional connectivity in the resting brain: A network analysis of the default mode hypothesis," PNAS, vol. 100, No. 1, pp. 253-258 (2003).
Sochat et al., "A Robust Classifier to Distinguish Noise from fMRI Independent Components," PLOS ONE, vol. 9, No. 4, pp. 1-14 (2014).
Van Den Heuvel et al., "Exploring the brain network: A review on resting-state fMRI functional connectivity," European Neuropsychopharmacology, vol. 20, pp. 519-534 (2010).
Larkman et al., "Use of Multicoil Arrays for Separation of Signal from Multiple Slices Simultaneously Excited," Journal of Magnetic Resonance Imaging, vol. 13, pp. 313-317 (2001).
Mckeown et al., "Independent component analysis of functional MRI: what is signal and what is noise?," Current Opinion in Neurobiology, vol. 13, No. 5, pp. 620-629 (2003).
Beckmann et al., "Investigations into resting-state connectivity using independent component analysis," Phil. Trans. R. Soc. B, vol. 360, pp. 1001-1013 (2005).
FslWiki—FIX, screenshot from web.archive.org, Nov. 24, 2016.
Souza et al., "SIMA: Simultaneous Multislice Acquisition of MR Images by Hadamard-Encoded Excitation," Journal of Computer Assisted Tomography, vol. 12, No. 6, pp. 1026-1030 (1988).
Jafri et al., "Functional Classification of Schizophrenia Using Feed Forward Neural Networks," EMBS Annual International Conference, pp. 6631-6634 (2006).

\* cited by examiner

METHOD AND COMPUTER DIFFERENTIATING CORRELATION PATTERNS IN FUNCTIONAL MAGNETIC RESONANCE IMAGING

BACKGROUND OF THE INVENTION

Field of the Invention

The invention concerns techniques for evaluating image data from functional magnetic-resonance imaging, in particular techniques for differentiating correlation patterns of neurophysical events and false patterns within the framework of an independent component analysis.

Description of the Prior Art

Magnetic resonance imaging (MRI) can be used to analyze neurophysical events. MRI can be used to analyze functionally correlated regions of the brain (anatomical neural networks) with respect to neurophysical events. Anatomical neural networks can be visualized by identifying correlation patterns of neurophysical events. Herein, correlation patterns characterize a temporal and/or spatial correlation of neurophysical events.

One appropriate technique is functional MRI (fMRI). With fMRI, temporal changes to image contrast are depicted by suitable MRI measuring sequences. For example, it is possible observe a blood oxygenation level dependent contrast within the framework of fMRI, also known as BOLD contrast. This enables neurophysical events to be measured.

One special technique in fMRI is so-called resting-state fMRI (rsfMRI). With rsfMRI, account is taken of the time dependence between neurophysical events that are spaced apart in the spatial domain (functional connectivity), wherein the anatomical neural network is exposed to no external stimuli, or to no significant external stimuli. For example, with rsfMRI, the person under examination is not asked to perform any specific activities or think any specific thoughts (resting state).

With rsfMRI, extensive time series of three-dimensional image data are analyzed in order to investigate the mode of operation and correlations of cerebral activity in resting state. Accelerated imaging sequences enable a particularly high time resolution to be achieved. For example, a number of two-dimensional layers can be excited and read-out simultaneously in a region of interest of a person under examination. See, for example, Souza, S. P., et al. "SIMA: simultaneous multilayer acquisition of MR images by Hadamard-encoded excitation." Journal of computer assisted tomography 12.6 (1988): 1026-1030; and Setsompop, Kawin, et al. "Blipped-controlled aliasing in parallel imaging for simultaneous multilayer echo planar imaging with reduced g-factor penalty." Magnetic Resonance in Medicine 67.5 (2012): 1210-1224; and Breuer, Felix A., et al. "Controlled aliasing in parallel imaging results in higher acceleration (CAIPIRINHA) for multi-layer imaging." Magnetic resonance in medicine 53.3 (2005): 684-691.

The higher time resolution results in an increased amount of MR data. The data set to be analyzed is larger, as a result of which the computing-intensive preprocessing of the image data requires significantly more time. Typical time series take approximately 6-8 minutes and can depict, for example, 700-1000 volume regions with 70-80 slices.

With rsfMRI, different techniques are used to evaluate the time series of image data. An evaluation is based on an independent component analysis (ICA). The ICA is conventionally based on model assumptions in dependence on the current data record, such as seed points, which control the evaluation a-priori or descriptions of an external stimulus. This means that the correlation patterns can be identified without an a-priori restriction. With an ICA, correlation patterns, which can explain the intensity changes in the time series of image data as the consequence of neurofunctional events, are sought in the underlying image data. An ICA finds candidate correlation patterns that are independent of one another. These are also referred to as components of an ICA. These multiple candidate correlation patterns include correlation patterns of the number of neurophysical events and false patterns, which are obtained, for example, due to noise in the image data or are inevitable result of the ICA algorithm used. The false patterns are often of subordinate interest and should be rejected.

With conventional rsfMRI techniques, it can be complicated to differentiate between the correlation patterns of the neurophysical events and the false patterns. For example, it may be necessary to classify a large number of candidate correlation patterns, identified by the ICA manually, as relevant correlation patterns of the neurophysical events or as false patterns. This can be time-consuming and susceptible to error.

Therefore, there is a need for improved techniques for MRI with respect to evaluating neurophysical events in the brain of a person under examination. There is a need for rsfMRI techniques that rectify or alleviate at least some of the aforementioned drawbacks and restrictions.

SUMMARY OF THE INVENTION

One method for MRI includes obtaining a time series of image data and providing the time series to a computer. The time series of image data depicts a number of neurophysical events in the brain of a person under examination in a spatially-resolved manner. The method further includes the performance of an ICA in the computer in order to identify a number of candidate correlation patterns based on the time series of image data. The multiple candidate correlation patterns include correlation patterns of the multiple neurophysical events, as well as false patterns, for example, intensity changes caused by noise or other effects such as physiological effects—heartbeat or respiration—or cause by the development of heat in the scanner. The method further includes the determination in the computer of a sub-region of the brain. The method further includes for each candidate correlation pattern in the multiple candidate correlation patterns, determining a corresponding value of a predetermined metric. The metric indicates an intensity of the respective candidate correlation pattern in the sub-region. The method further includes selection in the computer of at least one candidate correlation pattern from the multiple candidate correlation patterns based on the determined values of the predetermined metric. The method also includes flagging the at least one candidate correlation pattern selected for analysis by a user.

The aforementioned flagging can take place by generating and displaying an image of the brain of the subject in which areas of the brain that are correlated by the correlation pattern are displayed with the same appearance, such as the same color, in the overall displayed image of the brain.

The present invention also encompasses a magnetic resonance imaging apparatus having a control computer or control computer system that is configured to operate the magnetic resonance imaging apparatus in order to implement any or all embodiments of the method according to the invention, as described above.

The present invention also encompasses a non-transitory, computer-readable data storage medium encoded with programming instructions that, when the storage is loaded into a computer or computer system of a magnetic resonance imaging apparatus, cause the computer or computer system to operate the magnetic resonance imaging apparatus in order to implement any or all of the embodiments of the method according to the invention, as described above.

The use of an ANN to identify correlation patterns of neurophysical events of a neural network in a plurality of candidate correlation patterns is disclosed.

DESCRIPTION OF THE PREFERRED EMBODIMENTS

Figure 1:
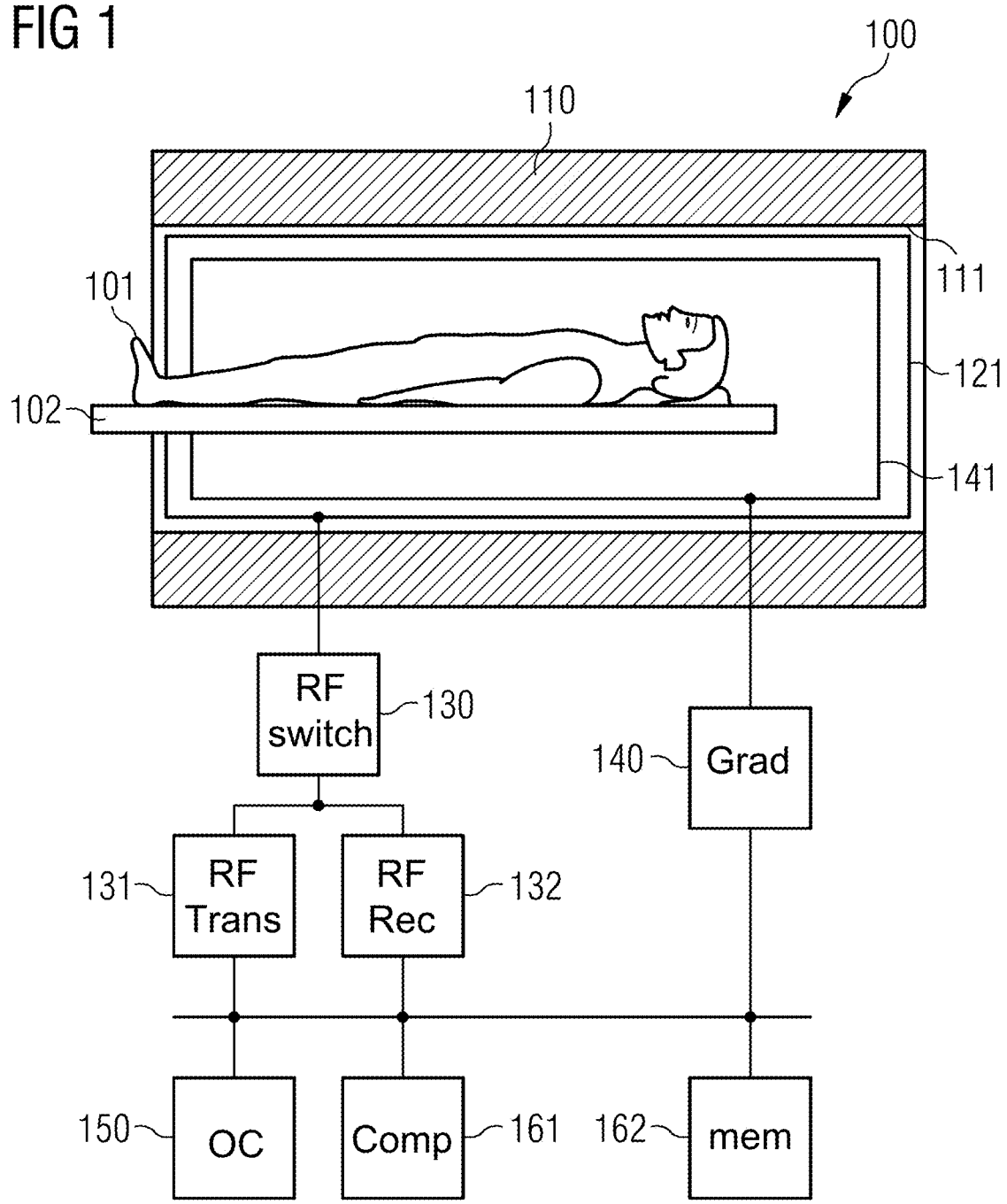
FIG. 1 schematically illustrates an MR system, which can be used for the rsfMRI techniques according to the invention.

The above-described properties, features and advantages of this invention and also the manner in which these are achieved will become clearer and more plainly comprehensible in conjunction with the following description of the exemplary embodiments explained in more detail in conjunction with the drawings.

The following describes the present invention in more detail on the basis of preferred embodiments and with reference to the drawings. In the figures, the same reference characters refer to the same or similar elements. The figures are schematic representations of different embodiments of the invention. Elements depicted in the figures are not necessarily shown true to scale. Rather, the various elements depicted in the figures are reproduced in such a way that their function and general purpose become comprehensible to the person skilled in the art. Connections and couplings between functional units and elements that are depicted in the figures may also be implemented as an indirect connection or coupling. A connection or coupling may be implemented in a wired or wireless manner. Functional units may be implemented as hardware, software or a combination of hardware and software.

Techniques for visualizing the functional connectivity of a neural network such as, for example, the brain of the person under examination are described below. The following describes techniques for identifying neurophysical events in the brain of a person under examination and associated correlation patterns. The techniques described herein enable the neurophysical events and the associated correlation patterns in the brain of the person under examination to be automated and identified particularly reliably. In particular, the techniques described may obviate the need for operators, such as medical personnel, having to manually annotate a number of candidate correlation patterns, which include both the correlation patterns of the multiple neurophysical events and false patterns, for example caused by noise includes, in order to differentiate the false patterns from the correlation patterns of the neurophysical events.

In various techniques described herein, a time series of image data is obtained that depicts an anatomical neural network three-dimensionally with suitable contrast. For example, the image data can be MR image data with BOLD contrast acquired by execution of an MR measurement sequence that acquires the time series of image data. For example, the MR measurement sequence can be image-accelerated, for example using SMS-techniques or undersampling of the spatial frequency domain. This enables a particularly high time resolution to be obtained so that the time series of image data has a particularly large number of time steps. Alternatively, acceleration of the measurement sequence can achieve increased spatial local resolution or a mixture of increased spatial and temporal resolution.

In the various techniques described herein, an ICA can then be performed based on the time series of image data. For example, various techniques described herein can obviate the need to establish a seed point with respect to a sub-region of the region of interest or the neural network before the ICA is performed. The ICA enables a large number of candidate correlation patterns to be obtained including both the actual correlation patterns of the neurophysical events—which depict the functional connectivity of the neural network—and false patterns, for example due to noise, signal changes for example due to the development of heat in the scanner, certain properties of the algorithm underlying the ICA and/or, for example, also intensity changes caused by physiological effects such as respiration or heartbeat. According to various techniques, it is possible to differentiate the correlation patterns of the neurophysical events from the false patterns in a targeted manner. In the various techniques described herein, it is possible for this differentiation to be performed fully automatically or largely automatically. For example, the techniques described herein can obviate the need for medical operators having to classify the set of candidate correlation patterns manually.

To this end, in different examples, a sub-region of the brain or the neural network generally is determined manually, semi-automatically or fully automatically. Then, a one-dimensional or multidimensional value of a predetermined metric is determined in a computer for each candidate correlation pattern obtained from the ICA. The metric can indicate the intensity of the respective candidate correlation pattern in the sub-region. It is then possible to select one or more candidate correlation patterns from the multiple candidate correlation patterns based on the values determined for the predetermined metric. For example, threshold-value comparisons with a predetermined threshold value can be implemented. Candidate correlation patterns with a particularly high intensity in the selected sub-region, for example compared to other candidate correlation patterns or compared to an absolute reference, can then be selected and flagged for analysis by a user.

The sub-region can be used to restrict the sample space of the ICA—which corresponds to the multiple candidate correlation patterns—to candidate correlation patterns with a significant intensity in the sub-region. For example, the sub-region can correspond to a region of interest (ROI) that is to be analyzed in more detail for diagnosis. Reducing the size of the sample space of the ICA, can greatly reduce the candidate correlation patterns to be checked by the user. For example, compared to the total number of candidate correlation patterns, the number of candidate correlation patterns selected on the basis of the metric can be no greater than 10%, optionally no greater than 5%, also optionally no greater than 1%.

In many examples, a suitable choice of metric can enable, when selecting the candidate correlation patterns based on the determined values of the predetermined metric, a differentiation between false patterns and correlation patterns of the neurophysical events to be made simultaneously. This means that a suitable choice of metric can also enable, with a particularly high degree of probability, the selection of only correlation patterns of the neurophysical events and thus achieve a differentiation between correlation patterns of the neurophysical events and false patterns.

In contrast to reference implementations, in techniques according to the invention the sub-region is not taken into account during the performance of the ICA. The sub-region can be taken in account only after the performance of the ICA. This means that the evaluation of the time series of image data is performed without an a-priori model assumption relating to a seed region.

A further example for the evaluation of the multiple candidate correlation patterns is based on the use of a suitably trained computer-implemented classifier. The classifier can achieve a differentiation between the false patterns and the correlation patterns of the plurality of neurophysical events. For example, an artificial neural network (ANN), such as an artificial convolutional neural network (CNN), can be used.

For example, the ANN can have a number of layers. For example, can the ANN can have an input layer, several hidden inter-layers and an output layer. The input layer can have a set of neurons, wherein the number of neurons corresponds to the number of image points of a candidate correlation pattern—or a component identified by the ICA. Then, the input layer can be transferred as an input feature map to the different candidate correlation patterns. The input layer can be connected to the output layer via several hidden interlayers. In the output layer, a corresponding neuron can exist for each category to be classified, wherein the neuron supplies the association of each transferred candidate correlation pattern with the respective category as an output feature map.

Different types of differentiation can be performed in the different examples described herein. For example, in a simple implementation, the output layer can have two neurons, one for the correlation patterns of the neurophysical events and one for the false patterns. It is also possible to differentiate between more than only two classes. For example, the classifier can be additionally configured to differentiate between correlation patterns of neurophysical events caused by physiological events and correlation patterns of spontaneous neurophysical events. This means that it is possible to differentiate between neurophysical events caused, for example, by heartbeat or respiration and associated correlation patterns and other neurophysical events and associated correlation patterns by means of the classifier.

Furthermore, it is also possible for the classifier to be additionally configured to differentiate between correlation patterns of different types of spontaneous neurophysical events. For example, the correlation patterns of the different spontaneous neurophysical events can be classified according to the regions of the brain with a particularly large corresponding intensity.

FIG. 1 is a schematic illustration of an MR system 100 that can be used to carry out the above-described techniques and the techniques described below. The MR system 100 has a scanner 110 that defines a tube 111. The scanner 110 generates a basic magnetic field parallel to its longitudinal axis.

An object under examination, here a person 101, can be moved into the scanner 110 on a support table 102. A region of interest of the person can be taken into account during the MR imaging. In the example in FIG. 1, the region of interest is in the region of the head of the person 101 in particular in the brain. The brain forms an anatomical neural network, and neurophysical events of the brain are to be visualized.

The scanner 110 furthermore has a gradient system 140 that generates gradient fields that spatially encode the MR signals emitted by excited nuclear spins, in order to produce raw MR data. The gradient system 140 typically has at least three gradient coils 141 that can be activated separately, and that are positioned in a well-defined manner relative to one another. The gradient coils 141 enable gradient pulses to be applied along certain spatial directions (gradient axes), which generate gradient fields. These gradient axes define a scanner coordinate system. The gradient fields can be used, for example, for slice selection, frequency encoding (in the readout direction) and phase encoding. This enables spatial encoding of the MR data to be achieved.

An RF coil arrangement 121 radiates an amplitude-modulated or frequency-modulated RF excitation pulse into the person 101. This gives the excited nuclear spins a transverse magnetization that causes the nuclear spins to deviate from the field lines of the basic magnetic field by an amount known as a flip angle. As these excited nuclear spins relax and return to the steady state, they emit radio-frequency signals, called MR signals. These MR signals are detected by the same RF antenna or antennas from which the excitation pulses were emitted, or by a different RF antenna. To generate such RF excitation pulses, an RF transmission system 131 is connected to the RF coil arrangement 121 via an RF switch 130. The RF transmission system 131 can include an RF generator and an RF amplitude modulation unit. The RF excitation pulses can deflect the transverse magnetization slice-selectively in 1D or spatially selectively or globally in 2D/3D out of the steady state. Alternatively or additionally to the RF excitation pulses, it is also possible to radiate RF refocusing pulses. It is then possible, for example in the case of SMS measurement sequences, for the transverse magnetization to be modified in several slices simultaneously.

Furthermore, an RF reception system 132 is coupled to the RF coil arrangement 121 via the RF switch 130. MR signals of the relaxing transverse magnetization can be acquired or measured with the use of the RF reception system 132 as MR data, for example, by inductive injection into the RF coil arrangement 121. With an SMS measurement sequence, the MR data can be obtained from more than one slice simultaneously.

The MR data are present as raw data in the spatial frequency domain. When using image-accelerated MR measurement sequences, there can be undersampling of the spatial frequency domain. In such cases, it may be necessary to reconstruct the MR data or to complete the MR data and then transform it into the image domain to obtain image data. A computer 161 of the MR system 100 is configured to perform these functions.

The MR system 100 furthermore has an operating console 150, which can, for example, include a monitor, a keyboard, a mouse etc. User inputs can be acquired and output to the user by means of the operating console 150. For example, it is possible for individual operating modes or operating parameters of the MR system 100 to be set by the user and/or automatically and/or via remote control by means of the operating console 150.

The MR system 100 also has the computer 161. For example, the computer 161 can be a processor, a microprocessor or a microcontroller. It would also be possible for the computer 161 to be a field-programmable gate array (FPGA) or an application-specific integrated circuit (ASIC). The MR system 100 further has a memory 162. Control instructions can be stored in the memory 162, so the control instructions can be executed by the computer 161. The execution of the control instructions by the computer 161 causes the computer 161 to carry out various techniques so as to enter the spatially encoded MR data into a memory organized as k-space according to different examples described herein.

The execution of the control instructions by the computer 161 causes the computer 161 to carry out various techniques. For example, the computer 161 can carry out techniques with respect to SMS imaging and with respect to the post-processing of a time series of image data in conjunction with rsfMRI. For example, the computer 161 can carry out techniques with respect to an ICA to identify a number of candidate correlation patterns, which include correlation patterns of neurophysical events and false patterns. For example, the computer 161 can then carry out techniques in order to differentiate the false patterns from the correlation patterns of the neurophysical events from the components or candidate correlation patterns identified by the ICA. To this end, the computer 161 can apply a computer-implemented classifier and/or a metric, which indicates an intensity the different candidate correlation patterns in a sub-region of the brain.

Figure 2:
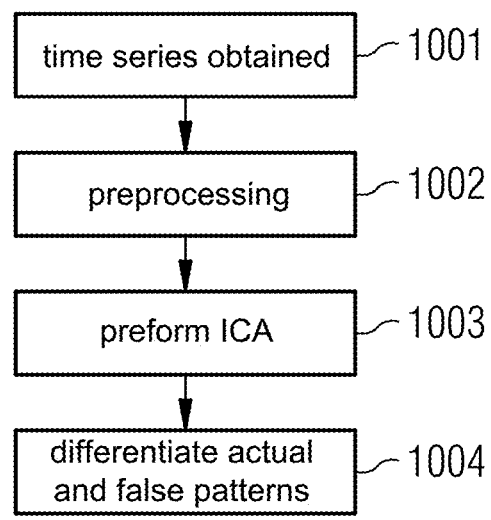
FIG. 2 is a flowchart of an embodiment of the method according to the invention.

FIG. 2 is a flowchart of an exemplary method. For example, the method according to FIG. 2 is performed by the computer 161.

First, in 1001 a time series of image data is obtained. For example, in 1001 an MR measurement sequence could be performed in order to obtain raw data with BOLD contrast. For example, the MR measurement sequence could include SMS imaging with undersampling of the spatial frequency domain and simultaneous excitation and reading out of several slices. For example, in 1001 undersampled raw data could be reconstructed, for example with techniques for partial parallel acquisition, such as GRAPPA: Griswold, Mark A., et al. "Generalized autocalibrating partially parallel acquisitions (GRAPPA)." Magnetic resonance in medicine 47.6 (2002): 1202-1210.

In 1002, different steps for preprocessing can be performed. 1002 is optional.

For example, within the framework of preprocessing, a movement of the person under examination can be compensated. For example, compensation can take place in the sub-voxel range. For example, it would be possible for rigid motion correction can be performed. See, for example, Thesen, Stefan, et al. "Prospective acquisition correction for head motion with image-based tracking for real-time fMRI." Magnetic Resonance in Medicine 44.3 (2000): 457-465.

A further aspect of the preprocessing can, for example, relate to normalization of the contrast in the image data. This enables compensation of temporal drifts of the amplitude of the contrast.

A further technique that can be considered in conjunction with the preprocessing of the image data relates to filtering of the temporal course of the contrast, for example for individual voxels of the image data. For example, temporal bandpass filtering could be performed. Typically, in conjunction with rsfMRI, a frequency of the observed signal changes lies within a special frequency band, for example in the region of from 8 MHz to 150 MHz. See, for example, Greicius, Michael D., et al. "Regional analysis of hippocampal activation during memory encoding and retrieval: fMRI study." Hippocampus 13.1 (2003): 164-174.

A further technique that can be considered in conjunction with the preprocessing in 1001 relates to spatial filtering. For example, a Gaussian kernel with a half-width of 3-4 mm can be applied. This enables signal artifacts to be reduced.

It is also possible for temporal correction of the image data depicting the different layers in the brain to be performed within the framework of preprocessing. For example, it is possible to compensate the time delay between the acquisition of MR data in different slices.

The above-described examples of techniques that are described within the framework of preprocessing 1002 are cited as examples. In other examples it would be possible, to apply the techniques described above in isolation only or to apply other techniques for preprocessing the image data in 1002.

This is followed in 1003 by the performance of the ICA. The ICA is used as the basis for identifying a plurality of candidate correlation patterns. The candidate correlation patterns correspond to independent components identified by the ICA. Superimposition of the independent components enables the time series of image data to be described. Each candidate correlation pattern can, for example, indicate a specific intensity in different voxels of the image data. Each candidate correlation pattern can be associated with a certain time dependence of an underlying signal pattern. Herein, in principle different voxels that contribute to a candidate correlation pattern can have the signal pattern that are phase shifted with respect to one another in the same or complementary manner or in some other way.

For example, within the framework of an ICA, the signal pattern of the different voxels of the time series of image data can be described as a linear combination of different components. Each time point can correspond, for example, to an observation. Herein, the number of time points can, therefore, indicate the number of observations that are generated from a specific different number of components. In other words, the ICA can be configured to identify a mixture of underlying components that describe the measured image data.

The ICA provides components with a maximum degree of independence from one another. The ICA can be applied to the entire measuring ranges resolved for different voxels. Details about the ICA in conjunction with the resting state fMRI are, for example, described in: Beckmann, Christian F., et al. "Investigations into resting-state connectivity using independent component analysis." Philosophical Transactions of the Royal Society of London B: Biological Sciences 360.1457 (2005): 1001-1013. Herein, the number of actual sources, i.e. the correlation patterns of actual neurophysical events, is not necessarily the same as the number of candidate correlation patterns that are identified as components within the framework of an ICA.

Therefore, in 1004, false patterns and correlation patterns of the neurophysical events are differentiated based on the plurality of candidate correlation patterns identified by the ICA.

Figure 3:
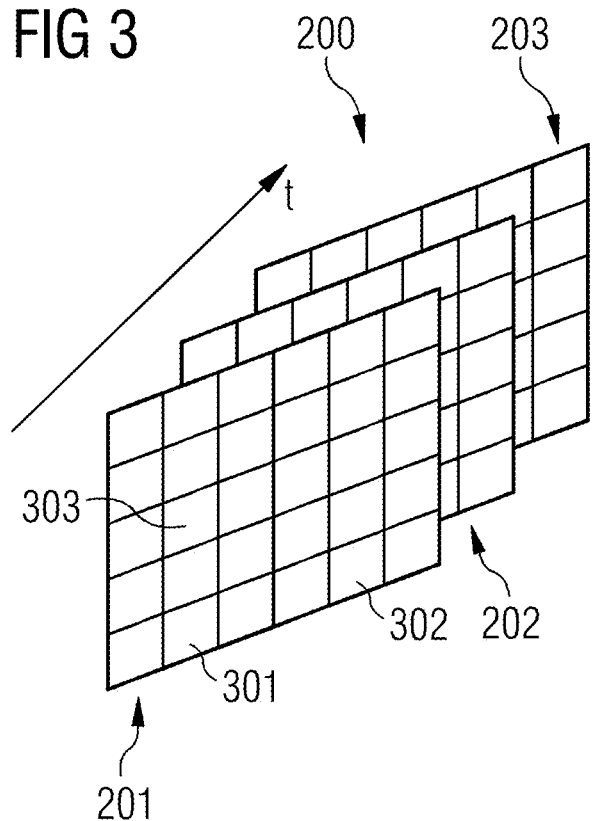
FIG. 3 illustrates a time series of image data, which was obtained the according to different examples by an MR image sequence with BOLD contrast.

FIG. 3 illustrates aspects with respect to a time series 200 of image data 201-203. FIG. 3 shows that different image data 201-203 is obtained at different time points. FIG. 3 shows an example in which two-dimensional image data 201-203 for a specific slice of a region of interest is obtained at different time points in each case. However, in other examples, it is possible for three-dimensional image data 201-203 depicting a three-dimensional region of interest, for example the brain of a person under examination, to be obtained for each time point in each case.

Herein, each image point of the image data can have a contrast corresponding to a signal integrated in a voxel of the region of interest. The contrast can, for example, be a BOLD contrast.

The image data 201-203 can, for example, be obtained with an MR measurement sequence. The image data 201-203 can, for example, be suitably preprocessed, for example in step 1002 according to the method from FIG. 2.

In FIG. 3, three image points 301-303 are highlighted.

Figure 4:
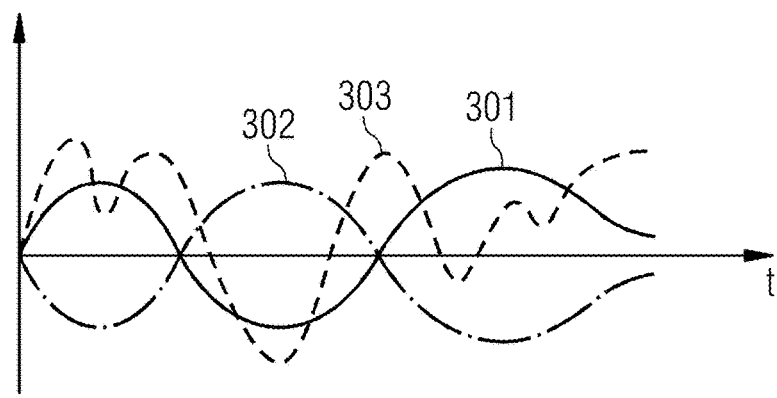
FIG. 4 schematically illustrates a temporal course of the contrast in different voxels of the image data according to different examples.

FIG. 4 illustrates aspects with respect to a temporal signal pattern of the contrast in the image points 301-303. It is evident from FIG. 4 that the contrast in the image points 301-303 varies as a function of time. The number of time points for which the contrast in the different image points is available is often also referred to as the number of observations. Therefore, each time point can represent an observation. With accelerated imaging, the time resolution and hence the number of observations can be particularly large.

For example, in FIG. 4, the contrast in the image point 301 is highly correlated with the signal pattern of the contrast in the image point 302. This is the case because the signal pattern in the image point 301 is embodied in phase opposition to the signal pattern in the image point 302. On the other hand, the signal pattern in the image point 303 is not particularly highly correlated with the signal patterns in the image points 301, 302. Therefore, it is possible to identify within the framework of the ICA that the signal patterns in the image points 301, 302 contribute to a common candidate correlation pattern.

Figure 5:
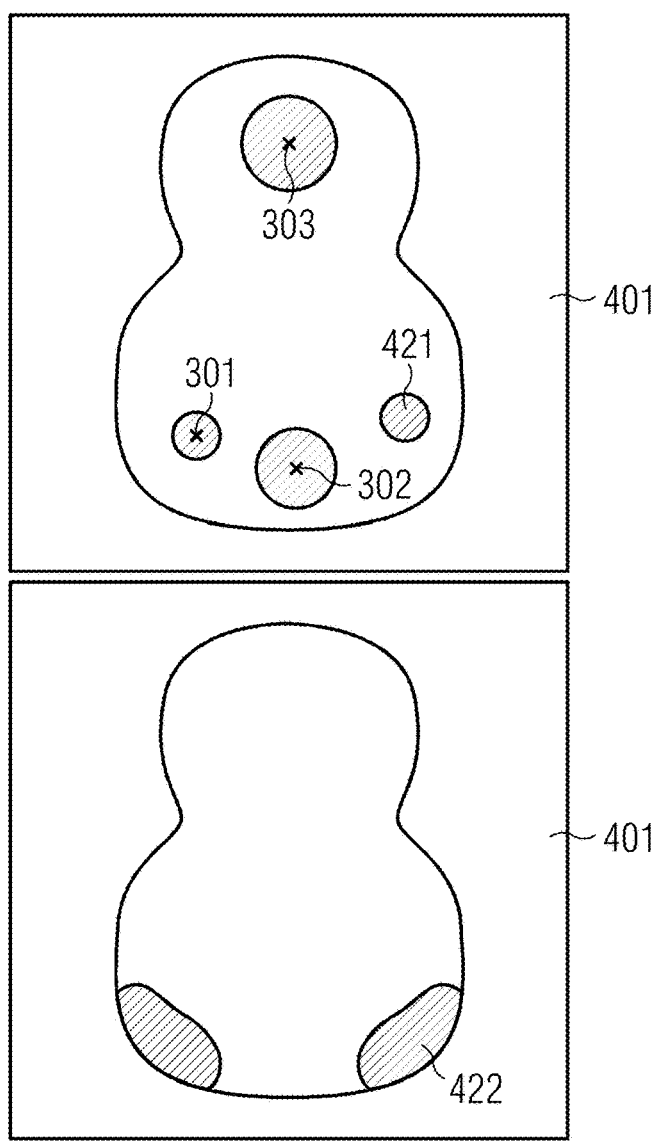
FIG. 5 schematically illustrates different candidate correlation patterns corresponding to components of an ICA, which is performed based on image data of the brain, according to different examples.

FIG. 5 illustrates aspects with respect to the results of the ICA. FIG. 5 shows an image 401 depicting a slice of the brain. FIG. 5 shows a transverse section through the brain.

Threshold-filtered, spatially resolved intensities of different candidate correlation patterns 421, 422, that were identified by the ICA, are depicted superimposed on the image 401 (top and bottom in FIG. 5). The intensities can have positive and negative values. Herein, the candidate correlation patterns 421, 422 correspond to different components of the ICA.

FIG. 5 depicts two candidate correlation patterns 421, 422 representing correlation patterns of actual neurophysical events. For example, the correlation pattern 421 is the so-called default-mode network, see Van Den Heuvel, Martijn P., and Hilleke E. Hulshoff Pol. "Exploring the brain network: a review on resting-state fMRI functional connectivity." European neuropsychopharmacology 20.8 (2010): 519-534, FIG. 2. The correlation pattern 422 is the extrastriate visual, see ibid.

The candidate correlation patterns 421, 422 display a high intensity (hatched regions in FIG. 5) in disjoint regions of the brain. It is possible for candidate correlation patterns with significant intensity in overlapping regions of the brain to be identified (not shown in FIG. 5). Moreover, FIG. 5 depicts a scenario in which only two candidate correlation patterns 421, 422 are identified. However, it is generally possible for a significantly higher number of candidate correlation patterns to be identified. It is in particular possible for candidate correlation patterns to be identified which do not correspond to correlation patterns of the neurophysical events but which are instead false patterns, for example due to noise (not shown in FIG. 5). The following describes techniques that enable differentiation of correlation patterns of the neurophysical events from false patterns. For example, such techniques can be performed in the framework of 1004 in FIG. 2.

Such techniques can be performed in consideration of the fact that the ICA does not provide the candidate correlation patterns in a predetermined or deterministic sequence. It is also possible for the +/− sign of the correlation patterns not to vary deterministically. In addition, the number of candidate correlation patterns can be dependent on the number of observations. Therefore, with a particularly high number of observations, a large number of false events may be obtained. Such boundary conditions of the algorithm underlying the ICA can be described in the different examples described herein.

Figure 6:
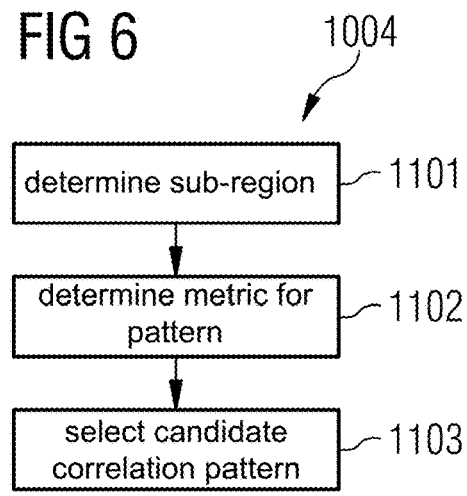
FIG. 6 is a flowchart of another embodiment of the method according to the invention.

FIG. 6 is a flowchart of an exemplary method. The method according to FIG. 6 can be used to differentiate between correlation patterns of the neurophysical events and false patterns based on a plurality of candidate correlation patterns, which were identified by an ICA. The method according to FIG. 6 can, for example, be performed in 1004 in FIG. 2.

Figure 7:
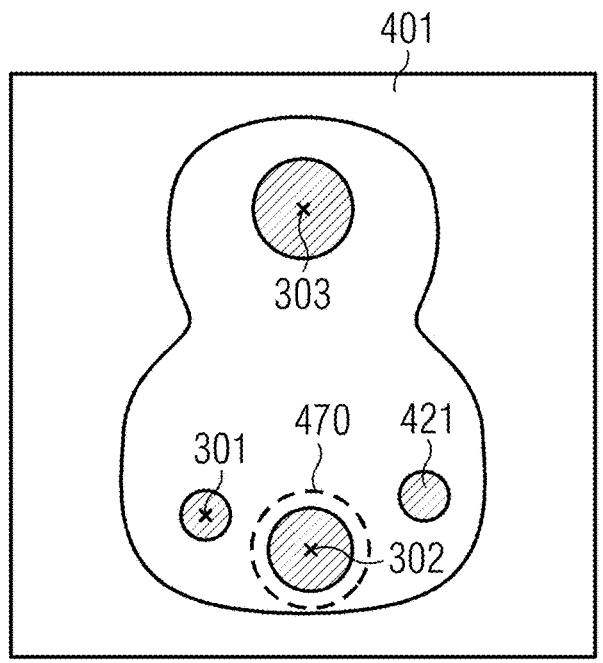
FIG. 7 schematically illustrates a sub-region defined according to different examples relating to the brain.

First, in 1101, a sub-region of the brain is determined (see FIG. 7 where a sub-region 470 of the brain is highlighted in the image 401 by the dashed line). In some examples, it would be possible for the sub-region 470 of the brain to be determined manually by a user. In other examples, it would also be possible for anatomical regions of the brain to be segmented based on the image data 201-203 or reference image data, which were, for example, obtained by a reference MR measurement sequence. Then, the sub-region can be determined based on the segmentation. For example, the segmentation could also include registration between the image data and reference image data, with which the anatomical regions are annotated. In other words, in 1101 the sub-region can be determined automatically. This can take place on a registration of an anatomical atlas. Herein, the user can, for example, select the relevant region in this case as a sub-region 470 from a list of known brain regions.

This is followed in 1102 by the determination of a, for example, one- or multidimensional value of a predetermined metric for each candidate correlation pattern that was previously identified by the ICA. Herein, the metric describes an intensity of the respective candidate correlation pattern in the sub-region.

This is followed by in 1103 by the selection of at least one candidate correlation pattern based on the determined values of the predetermined metric for the different candidate correlation patterns. For example, in 1103, it would be possible to select candidate correlation patterns selected with a particularly high or a particularly low intensity, the in the sub-region. To this end, it is possible for a threshold-value comparison to be performed. Selected candidate correlation patterns can then be flagged for analysis by a user. For example, selected candidate correlation patterns can be provided as an output via the user interface. The user can thereby obtain a sorted list of candidate correlation patterns, wherein the list is sorted according to the determined values of the predetermined metric in each case.

Such techniques can achieve a reduction of the sample space that has to be analyzed by the user. It is possible to achieve filtering with respect to candidate correlation patterns that are relevant with respect to the sub-region 470—for example a ROI.

Herein, it should be noted that the ICA is performed in a region of the brain that encloses the sub-region and is larger than the sub-region 470, or is performed in the whole brain. In other words, the selection of the sub-region does not influence the performance of the ICA. In contrast to reference implementations, therefore, the selected sub-region 470 is not used as a basis for identifying the candidate correlation patterns. Instead, the sub-region 470 is only used following the ICA, namely to support a differentiation of false patterns from correlation patterns of the neurophysical events.

A suitable choice of metric can assist in the accurate differentiation between correlation patterns of the neurophysical events and false patterns. This can be assisted by taking into account the properties of the components extracted by the ICA when selecting the metric. For example, many techniques for selecting the metric are based on the knowledge that the ICA determines the candidate correlation patterns in a non-deterministic sequence and also with a variable variance and variable +/− sign. Therefore, in many examples, it can be possible for the metric to take account of a normalized variance of a component of the time series of image data that corresponds to the respective candidate correlation pattern.

The metric can take account of an intensity of a component of the time series 200 of image data 201-203 corresponding to the respective candidate correlation pattern that is integrated over the sub-region 470. For example, the metric could take account of an integrated intensity of the normalized variance of a component as an integral over the sub-region 470. Herein, the sub-region 470 can, for example, be defined as two-dimensional or three-dimensional; and the integral can correspondingly be defined as two-dimensional or three-dimensional.

It is also possible for the metric to take account of a contribution of the intensity of a component of the time series 200 of image data 201-203 corresponding to the respective candidate correlation pattern. This means that the +/− sign for the intensity of a respective candidate correlation pattern can be left out of consideration. Thus, any +/− sign obtained by the ICA for the different components can be compensated during the determination of the intensity of the corresponding candidate correlation pattern in the sub-region 170. This is based on the knowledge that the +/− sign for the intensity of the different candidate correlation patterns often has no physically relevant content.

In many examples, the metric can take account of a difference between intensities of a component of the time series 200 of image data 201-203 corresponding to the respective candidate correlation pattern inside and outside the sub-region 470. Thus, it is possible to identify candidate correlation patterns with a particularly uniform intensity inside and outside the sub-region 470. Such candidate correlation patterns can be identified as false patterns because they are caused as a result of noise and are activated uniformly in the region of the brain or over extended regions of the brain and not restricted to an anatomically relevant sub-region 470. Thus, it is possible for particularly efficient differentiation between false patterns and correlation patterns of the neurophysical events to take place.

Therefore, techniques such as those described with respect to the method according to FIG. 6 enable the automated identification of correlation patterns of the neurophysical events based on a number of candidate correlation patterns that also include false patterns. In particular, it is also possible for such an identification to take place without the error-susceptible and time-consuming manual definition of seed regions as an a-priori restriction. A sub-region can be taken into account following the performance of the ICA. Herein, the consistency of the identified correlation patterns of the neurophysical events can be higher than manually defined seed regions as an a-priori restriction since the ICA does not, for example, generate any inconsistent "mixed regions". For example, in reference techniques based on a seed point as an a-priori restriction, it is possible, to define a seed region that, anatomically and from viewpoints of connectivity, does not form an individually enclosed region. This greatly impairs the quality of the extracted components. In addition, the solution to this problem is not trivial since the result of the ICA is not yet available at the time of the determination of the seed regions. Such drawbacks are avoided by the techniques described herein.

In the techniques described herein it is possible to determine the candidate correlation patterns fully automatically by means of the ICA. In a step independent step thereof, it is possible for the user to specify a sub-region that is particularly relevant for the current analysis. Only then are these independent items of information linked to one another so that an imprecisely defined seed region as a-priori information for the ICA does not affect the quality of the results or does not affect it significantly.

Figure 8:
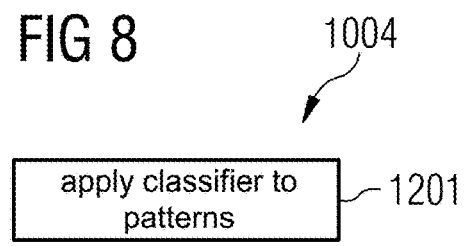
FIG. 8 is a flowchart of the method according to the invention according to different examples.

FIG. 8 is a flowchart of an exemplary method. In particular, FIG. 8 illustrates techniques with respect to the differentiation of correlation patterns of the neurophysical events from false patterns. For example, the method according to FIG. 8 could be performed within the framework of 1004 in FIG. 2.

In 1201, a computer-implemented classifier is applied to the plurality of candidate correlation patterns identified within the framework of an ICA. The classifier is configured to achieve a differentiation between the false patterns and the correlation patterns of the multiple neurophysical events.

Such effects are based on the knowledge that false patterns can frequently have a characteristic spatial domain profile for the intensity. For example, false patterns can have a characteristic spatial domain profile due to movement—for example caused by physiological effects such as respiration—or due to blood flow—for example caused physiological effects such as heartbeat. For example, due to movement, the spatial domain profile of false patterns can have a particularly high intensity at the circumference of the brain because opposite sides of the brain move in correlation. This knowledge enables false patterns to be identified particularly effectively by means of the computer-implemented classifier.

For example, an ANN can be used as a classifier. One example of an ANN is a CNN. Corresponding techniques are known in principle to the person skilled in the art from: Krizhevsky, Alex, Ilya Sutskever, and Geoffrey E. Hinton. "ImageNet Classification with Deep Convolutional Neural Networks." Advances in neural information processing systems. 2012 and Lawrence, Steve, et al. "Face recognition: A convolutional neural-network approach." IEEE transactions on neural networks 8.1 (1997): 98-113. With a CNN, spatially limited three-dimensional regions are convoluted with three-dimensional kernels. This means that a neuron in one slice is not fully linked to all the neurons in a preceding slice. Translation invariance is achieved in that each kernel is convoluted with all possible sensitive regions. The CNN can also support several hidden planes. Depending upon the number of planes used, it is possible to identify a different number of features in the input data, i.e. the image data provided by the ICA, that depicts the candidate correlation patterns. Simultaneously, the number of parameter is reduced. It is also possible to use pooling-layers that consolidate the results of preceding layers. It is also possible for fully connected layers to be used, typically close to the output layer.

The training of an ANN can be based on techniques that are known in principle. For example, it is possible to use the backward propagation algorithm, see Rumelhart, David E., Geoffrey E. Hinton, and Ronald J. Williams. "Learning representations by back-propagating errors." Cognitive modeling 5.3 (1988): 1. This typically requires a set of known training pairs from an ICA compared to categories. The categories are assigned manually, for example, by an experienced user. The result of the training is then available in a set of edge weights for the corresponding ANN, which characterize the respective weighting of the data on passage through the ANN from the input layer to the output layer. When the ANN has been trained, typically no further interaction is required for the classification of the components of the ICA or the candidate correlation patterns. The set of components of the ICA can then be classified iteratively by the ANN.

Different categories acquired by the classifier are conceivable in different examples. For example, the different categories can be learned by suitable training of the classifier. The classifier could be configured to differentiate between correlation patterns of different types of spontaneous neurophysical events. Examples of correlation patterns of spontaneous neurophysical events include for example "Default Mode Network", "Attention Network", etc. The correlation patterns of different types of spontaneous neurophysical events are for example described in: Greicius, Michael D., et al. "Functional connectivity in the resting brain: a network analysis of the default mode hypothesis." Proceedings of the National Academy of Sciences 100.1 (2003): 253-258.

The techniques described herein can also be used for the automated selection of relevant correlation patterns of neurophysical events based on computer-implemented classification of components of an ICA corresponding to candidate correlation patterns. There is no manual selection. This greatly simplifies user interaction in conjunction with rsf-MRI.

The various techniques described herein can, for example, be performed by a computer 161 of the MR system 100. However, it would also be possible to use cloud computing. For example, the candidate correlation patterns could be transferred to a server and the server could then be configured to differentiate between the correlation patterns of the neurophysical events and false patterns.

The features of above-described embodiments and aspects of the invention can be combined with one another. In particular, the features can be used not only in the described combinations but also in other combinations or for on their own without departing from the scope of the invention.

For example, in the above, different examples were described in which the image data was obtained from MRI. This is by way of example and in other examples it would also be possible for other imaging techniques to be used.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for magnetic resonance (MR) imaging, comprising:
    operating an MR data acquisition scanner in order to acquire a time series of raw MR data that represent a plurality of spatially-resolved neurophysical events in the brain of a subject;
    in a computer, reconstructing image data from said raw MR data depicting the brain with said spatially-resolved neurophysical events therein;
    in said computer, performing an independent component analysis (ICA) in order to identify a plurality of candidate correlation patterns among said plurality of neurophysical events, said plurality of candidate correlation patterns comprising actual correlation patterns of said plurality of neurophysical events and false patterns;
    in said computer, applying a classifier to said plurality of candidate correlation patterns that differentiates between said false patterns and said actual correlation patterns of said plurality of neurophysical events, thereby producing a differentiated set of correlation patterns of said plurality of neurophysical events; and
    using said differentiated set of correlation patterns of said plurality of neurophysical events to display an image of the brain of the subject, at a display in communication with said computer, wherein areas of the brain comprising neurophysical events that are correlated with each other are shown in said display with a same display appearance.

2. A method as claimed in claim 1 comprising classifying said plurality of candidate correlation patterns using an artificial neural network.

3. A method as claimed in claim 2 comprising using an artificial convolution neural network as said artificial neural network.

4. A method as claimed in claim 2 wherein the artificial neural network comprises an input layer, a plurality of hidden inter-layers, and an output layer, the output layer including a first neuron for the actual correlation patterns of the neurophysical events and a second neuron for the false patterns.

5. A method as claimed in claim 1 comprising classifying said plurality of candidate correlation patterns to additionally differentiate between correlation patterns of different types of spontaneous neurophysical events, among said plurality of neurophysical events.

6. A magnetic resonance (MR) apparatus comprising:
    an MR data acquisition scanner; and
    a computer configured to:
        operate an MR data acquisition scanner in order to acquire a time series of raw MR data that represent a plurality of spatially-resolved neurophysical events in the brain of a subject;
        reconstruct image data from said raw MR data depicting the brain with said spatially-resolved neurophysical events therein;
        perform an independent component analysis (ICA) in order to identify a plurality of candidate correlation patterns among said plurality of neurophysical events, said plurality of candidate correlation patterns comprising actual correlation patterns of said plurality of neurophysical events and false patterns;
        apply a classifier to said plurality of candidate correlation patterns that differentiates between said false patterns and said actual correlation patterns of said plurality of neurophysical events, thereby producing a differentiated set of correlation patterns of said plurality of neurophysical events; and use said differentiated set of correlation patterns of said plurality of neurophysical events to display an image of the brain of the subject, at a display in communication with said computer, wherein areas of the brain comprising neurophysical events that are correlated with each other are shown in said display with a same display appearance.

7. An apparatus as claimed in claim 6 wherein the computer is further configured to classify said plurality of candidate correlation patterns using an artificial neural network, wherein the artificial neural network comprises an input layer, a plurality of hidden inter-layers, and an output layer, the output layer including a first neuron for the actual correlation patterns of the neurophysical events and a second neuron for the false patterns.

8. A non-transitory, computer-readable data storage medium encoded with programming instructions, said storage medium being loaded into a computer system of a magnetic resonance (MR) apparatus comprising an MR data acquisition scanner, said programming instructions causing said computer system to:

operate said MR data acquisition scanner in order to acquire a time series of raw MR data that represent a plurality of spatially-resolved neurophysical events in the brain of a subject;

reconstruct image data from said raw MR data depicting the brain with said spatially-resolved neurophysical events therein;

perform an independent component analysis (ICA) in order to identify a plurality of candidate correlation patterns among said plurality of neurophysical events, said plurality of candidate correlation patterns comprising actual correlation patterns of said plurality of neurophysical events and false patterns;

apply a classifier to said plurality of candidate correlation patterns that differentiates between said false patterns and said actual correlation patterns of said plurality of neurophysical events, and thereby produce a differentiated set of correlation patterns of said plurality of neurophysical events; and use said differentiated set of correlation patterns of said plurality of neurophysical events to display an image of the brain of the subject, at a display in communication with said computer, wherein areas of the brain comprising neurophysical events that are correlated with each other are shown in said display with a same display appearance.

9. A storage medium as claimed in claim 8 wherein said programming instructions cause said computer system to classify said plurality of candidate correlation patterns using an artificial neural network, wherein the artificial neural network comprises an input layer, a plurality of hidden inter-layers, and an output layer, the output layer including a first neuron for the actual correlation patterns of the neurophysical events and a second neuron for the false patterns.

* * * * *